United States Patent [19]

Begany et al.

[11] 4,097,596

[45] Jun. 27, 1978

[54] INHALATION THERAPY FOR RELIEVING BRONCHIAL SPASM USING QUATERNARY SALTS OF PROMETHAZINE

[75] Inventors: Albert J. Begany, Tucson, Ariz.; Marvin E. Rosenthale, Havertown; Alphonse Dervinis, Wayne, both of Pa.

[73] Assignee: American Home Products Corporation, New York, N.Y.

[21] Appl. No.: 737,927

[22] Filed: Nov. 2, 1976

[51] Int. Cl.$^2$ .............................................. A61K 31/54
[52] U.S. Cl. ....................................... 424/247; 424/45
[58] Field of Search ................................... 424/45, 247

[56] References Cited

U.S. PATENT DOCUMENTS 2,887,481  5/1959  Sherlock et al. ..................... 260/243
3,671,625  6/1972  Altounyan ............................. 424/45

OTHER PUBLICATIONS

Remington's Pharmaceutical Sciences, 13th Ed., 1965, p. 1208.
Remington's Pharmaceutical Sciences, 13th Ed., 1965, p. 450.
Merck Index, 9th Ed., 1976, p. 1201.
Chemical Abstracts 45:2511i (1951), (abstract of British Pat. No. 641,452).

Primary Examiner—Leonard Schenkman
Attorney, Agent, or Firm—Robert Wiser

[57] ABSTRACT

The use of quaternary salts of promethazine by the inhalation route is described. The thus administered compositions provide new, non-toxic, potent means for relieving bronchial spasm and bronchoconstriction in warm-blooded animals.

16 Claims, No Drawings

INHALATION THERAPY FOR RELIEVING BRONCHIAL SPASM USING QUATERNARY SALTS OF PROMETHAZINE

BACKGROUND OF THE INVENTION

There are at present several commercially available inhalation preparations useful for the treatment of asthma, bronchial spasm, and reversible bronchoconstriction. These preparations are either certain catacholamines in powder form or solution, or a solution of the adrenal cortical steroid, dexamethasone. For administration, the powder is sprayed or the solution is first atomized and then sprayed directly into the nasal or oral opening. In addition, there is an inhalable powder comprising a bis-chromone derivative; however, this medicament has no intrinsic bronchodilator, or anti-histamine activity, and is useful only prophylactically. It is not indicated for treating an acute asthmatic attack. The literature also describes the use of certain prostaglandins by the oral inhalation route for the relief of bronchial spasm. Thus, for example, Belgian Pat. No. 792,216 describes this use for prostaglandin $F_{2\beta}$. The use of certain quaternary salts of atropine as inhalable anticholinergic bronchodilators has been reported Arzneim. Forsch.(Drug Res.)26, 959–1020, (1976). The use of certain quaternized phenothiazines [e.g. 1-(10-phenothiazinylmethyl)ethyl-2-hydroxyethyldimethylammonium chloride, Acta. pharmacol. et toxicol., 18, 105(1961)] as antihistiminics (i.m. administration) has also been studied.

The existing inhalable medicaments useful for the control of asthma, bronchial spasm and similar disorders each, unfortunately, possess deleterious side effects and a generally useful medicament, indicated for use by all patients requiring inhalation therapy does not exist.

The catacholamines most often utilized are epinephrine, isoproterenol, and metaproterenol. These adrenergic agents are most powerful and useful drugs in the relief of severe asthmatic spasm (status asthmaticus); however, as with other dilators they have untoward side effects. Some of the more undesirable of these are stimulation of the cardiovascular and central nervous system, hyperglycemia and tolerance (tachyphylaxis), which greatly reduces the effectiveness of these drugs.

Many cases of asthma and status asthmaticus refractory to usual treatment methods may now be controlled by the use of inhalable dexamethasone. However, long term treatment of asthma with steroids involves the risk of sodium retention, hypertension, ulcers, calcium loss from osseous structures and other well-known side effects.

Thus, the agents presently available to the physician have a number of problems associated with their use, including toxicity, adverse effect on the cardiovascular system (especially in the sympathomimetics) and fluid retention or edema (with the corticosteroids). Thus, a definite need exists for means employing effective and well-tolerated bronchodilating agents.

The difficulty in finding such agents is well-known to those skilled in the art. It is a matter of common knowledge and experience, for example, that many compounds that relax smooth muscles are not bronchodilators by all common routes of administration (and especially by the aerosol route of administration). For example, for some obscure reason, ephedrine is a smooth muscle relaxant and is an orally active bronchodilator, but not by aerosol; epinephrine, also a smooth muscle relaxant, is used by aerosol but not orally. And aminophylline, a drug which can relax bronchial smooth muscle in vitro or by injection in vivo is inactive as a bronchodilator aerosol. In view of this it is surprising to find new means which, even though characterized by smooth muscle relaxing activity, provide bronchodilation by administration via the aerosol route, possess high levels of activity, and are non-toxic.

The present invention provides new, potent, bronchodilator compositions comprising quaternary salts of the well-known medicament, promethazine, which compositions are useful upon administration by the aerosol route.

SUMMARY OF THE INVENTION

The invention sought to be patented in its principal process aspect resides in the concept of a method of relieving bronchial spasm and facilitating breathing in warm-blooded animals which comprises administering to a warm-blooded animal in need thereof, by aerosol route, an amount sufficient to relieve bronchial spasm and facilitate breathing in said warm-blooded animal of a composition comprising:

(a) a compound of the formula:

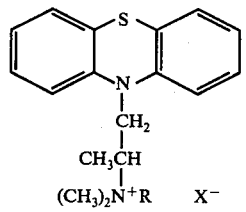

wherein R is cyclopropylmethyl or alkyl of from 1 to 4 carbon atoms; X is a pharmacologically acceptable anion; and (b) a pharmacologically acceptable carrier.

The invention sought to be patented in its first subgeneric process aspect resides in the concept of a method of relieving bronchial spasm and facilitating breathing in warm-blooded animals which comprises administering to a warm-blooded animal in need thereof, by aerosol route, an amount sufficient to relieve bronchial spasm and facilitate breathing in said warm-blooded animal of a composition comprising:

(a) a compound of the formula:

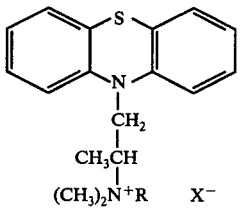

wherein R is cyclopropylmethyl or alkyl of from 1 to 4 carbon atoms; X is $OH^-$, $Cl^-$, $Br^-$, $I^-$, $NO^-_3$,

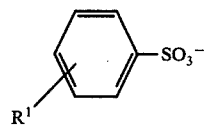

wherein $R^1$ is hydrogen, alkyl of from 1 to 6 carbon atoms, methoxy, chlorine, or bromine, $R^2SO^-_4$ wherein $R^2$ is alkyl of from 1 to 3 carbon atoms; and (b) a pharmacologically acceptable carrier.

The invention sought to be patented in its second subgeneric process aspect resides in the concept of a method of relieving bronchial spasm and facilitating breathing in warm-blooded animals which comprises administering to a warm-blooded animal in need thereof, by aerosol route, an amount sufficient to relieve bronchial spasm and facilitate breathing in said warm-blooded animal of a composition comprising:

(a) dl-trimethyl[1-methyl-2-(phenothiazin-10-yl)ethyl]ammonium iodide; and (b) a pharmacologically acceptable carrier.

The invention sought to be patented in its third subgeneric process aspect resides in the concept of a method of relieving bronchial spasm and facilitating breathing in warm-blooded animals which comprises administering to a warm-blooded animal in need thereof, by aerosol route, an amount sufficient to relieve bronchial spasm and facilitate breathing in said warm-blooded animal of a composition comprising:

(a) d-trimethyl[1-methyl-2-(phenothiazin-10-yl)ethyl]ammonium iodide; and (b) a pharmacologically acceptable carrier.

The invention sought to be patented in its fourth subgeneric process aspect resides in the concept of a method of relieving bronchial spasm and facilitating breathing in warm-blooded animals which comprises administering to a warm-blooded animal in need thereof, by aerosol route, an amount sufficient to relieve bronchial spasm and facilitate breathing in said warm-blooded animals of a composition comprising:

(a) l-trimethyl[1-methyl-2-(phenothiazin-10-yl)ethyl]ammonium iodide; and (b) a pharmacologically acceptable carrier.

The invention sought to be patented in its fifth subgeneric process aspect resides in the concept of a method of relieving bronchial spasm and facilitating breathing in warm-blooded animals which comprises administering to a warm-blooded animal in need thereof, by aerosol route, an amount sufficient to relieve bronchial spasm and facilitate breating in said warm-blooded animal of a composition comprising:

(a) trimethyl[1-methyl-2-phenothiazin-10-yl)ethyl]ammonium chloride; and (b) a pharmacologically acceptable carrier.

The invention sought to be patented in its principal composition aspect resides in the concept of a bronchodilating and spasm reducing composition formulated for inhalation therapy from a nebulizer such that each dose comprises:

(a) a bronchodilating and bronchial spasm reducing amount of a compound of the formula:

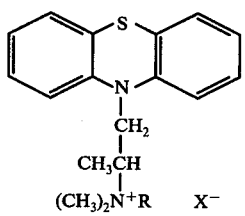

wherein R is cyclopropylmethyl or alkyl of from 1 to 4 carbon atoms; X is a pharmacologically acceptable anion; and (b) a pharmacologically acceptable inhalation carrier, in an amount sufficient to provide a composition administerable by the oral inhalation route.

The invention sought to be patented in its first subgeneric composition aspect resides in the concept of a bronchodilating and bronchial spasm reducing composition formulated for inhalation therapy from a nebulizer such that each dose comprises:

(a) a bronchodilating and bronchial spasm reducing amount of a compound of the formula:

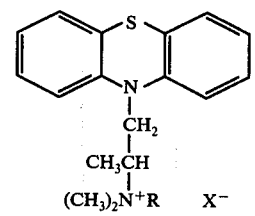

wherein R is cyclopropylmethyl or alkyl of from 1 to 4 carbon atoms; X is $OH^-$, $Cl^-$, $Br^-$, $I^-$, $NO^-_3$,

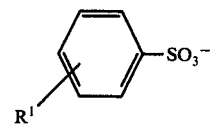

wherein $R^1$ is hydrogen alkyl of from 1 to 6 carbon atoms, methoxy, chlorine, or bromine, $R^2SO^-_4$, wherein $R^2$ is alkyl of from 1 to 3 carbon atoms; and (b) a pharmacologically acceptable inhalation carrier, in an amount sufficient to provide a composition administerable by the oral inhalation route.

The invention sought to be patented in its second subgeneric composition aspect resides in the concept of a bronchodilating and bronchial spasm reducing composition formulated for inhalation therapy from a nebulizer such that each dose comprises:

(a) a bronchodilating and bronchial spasm reducing amount of dl-trimethyl [1-methyl-2-(phenothiazin-10-yl)ethyl]ammonium iodide; and (b) a pharmacologically acceptable inhalation carrier, in an amount sufficient to provide a composition administerable by the oral inhalation route.

The invention sought to be patented in its third subgeneric composition aspect resides in the concept of a bronchodilating and bronchial spasm reducing composition formulated for inhalation therapy from a nebulizer such that each dose comprises:

(a) a bronchodilating and bronchial spasm reducing amount of d-trimethyl[1-methyl-2-(phenothiazin-10-yl)ethyl]ammonium iodide; and (b) a pharmacologically acceptable inhalation carrier, in an amount sufficient to provide a composition administerable by the oral inhalation route.

The invention sought to be patented in its fourth subgeneric composition aspect resides in the concept of a bronchodilating and bronchial spasm reducing composition formulated for inhalation therapy from a nebulizer such that each dose comprises:

(a) a bronchodilating and bronchial spasm reducing amount of l-trimethyl[1-methyl-2-(phenothiazin-10-yl)ethyl]ammonium iodide; and (b) a pharmacologically acceptable inhalation carrier, in an amount sufficient to provide a composition administerable by the oral inhalation route.

The invention sought to be patented in its fifth subgeneric composition aspect resides in the concept of a bronchodilating and bronchial spasm reducing composition formulated for inhalation therapy from a nebulizer such that each dose comprises:

(a) a bronchodilating and bronchial spasm reducing amount of trimethyl[1-methyl-2-(phenothiazin-10-yl)ethyl]ammonium chloride; and (b) a pharmacologically acceptable inhalation carrier, in an amount sufficient to provide a composition administerable by the oral inhalation route.

DESCRIPTION OF THE INVENTION

The quaternary salts of promethazine utilized in the processes and compositions of the instant invention may be conveniently prepared, for example, from promethazine itself or from 10-(2-aminopropyl)phenothiazine (U.K. Pat. No. 731,016) by methods familiar to those skilled in the art (see for example, U.K. Pat. No. 641,452). Many of the salts contemplated by the instant invention may be prepared, conveniently, by mixing a solution of promethazine and the salt forming reagent in a solvent in which both materials will be soluble and in which the product quaternary salt will be insoluble. The product salt is then easily collected by filtration. Examples of such solvents are acetone, benzene, ether and the like. The salt, in most cases, will form spontaneously at room temperature but in certain instances heating for several hours (e.g. about 8 hours) may be required. Those skilled in the art will readily be able to ascertain those instances when heating is required. The use of methods other than that described above for preparing and isolating quaternary salts is also contemplated. Thus a solvent may be employed in which promethazine, the salt forming reagent and the quaternary salt may all be substantially soluble (e.g. ethanol). In this instance, after reaction, the salt may be collected by, for example, concentration or evaporation of the solvent and it may be purified by, for example, recrystallization. Other methods will suggest themselves to those skilled in the art.

The salt forming reagents contemplated by the invention are those of the general formula R—Y wherein R is cyclopropylmethyl or alkyl of from 1 to 4 carbon atoms; and Y is a pharmacologically acceptable anion. The alkyl radicals contemplated by the instant invention are methyl, ethyl, isopropyl, propyl, butyl, and the like. The anions contemplated by the instant invention are all of the pharmacologically acceptable, non-toxic anions known in the art. These anions will be familiar to those skilled in the art, and are exemplified by, for example, $OH^-$, $Cl^-$, $Br^-$, $I^-$, $NO^-_3$,

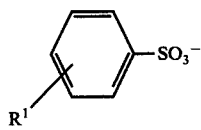

wherein $R^1$ is hydrogen, alkyl of from 1 to 6 carbon atoms, methoxy, chlorine, or bromine, and $R^2SO^-_4$ wherein $R^2$ is alkyl of from 1 to 3 carbon atoms.

Examples of salt forming reagents contemplated by the instant invention are methyl iodide, isopropyl bromide, butyl iodide, cyclopropylmethyl bromide, dimethyl sulfate, methyl p-toluene sulfonate, methyl chloride and the like.

Certain anions may be introduced into the quaternary salt by an exchange process. Anion exchange methods will be familiar to those skilled in the art; for example, chromatographic means may be employed.

Promethazine itself, is a well-known medicament and its synthesis by several different methods has been described (see for example, U.S. Pat. Nos. 2,530,451; 2,607,773).

Because the promethazine molecule contains in its structure an assymetric carbon atom, the molecule is capable of existing as the d,l racemic mixture as well as in its pure d and pure l forms. Thus, the instant invention contemplates the quaternary salts of dl-promethazine as well as the quaternary salts of d-promethazine and the quaternary salts of l-promethazine. Methods for separating dl-promethazine into its enantiomeric constituents, substantially free from each other, will be familiar to those skilled in the art [see for example Toldy, L., et al., Acta. Chim. Acad. Sci. Hung., 19, 273 (1959); C. A. 3425[h] (1960)]. Methods for producing quaternary salts from either the d or l isomer are substantially identical to those methods useful for the d,l racemic mixture.

For purposes of this invention, a preferred quaternary salt of promethazine is the meth-chloride (dl-trimethyl[1-methyl-2-(phenothiazin-10-yl)ethyl]ammonium chloride). This salt is readily prepared by methods known to those skilled in the art. Thus for example, on mixing a solution of dl-promethazine and methyl chloride in a suitable solvent such as acetone at for example, reflux temperature, the quaternary meth-chloride salt is obtained as a precipitate which is easily collected by filtration. The salt obtained in this manner may be purified by, for example recrystallization, and is suitable for use in the method and compositions of the invention. Other favored quaternary salts are the meth-iodide, meth-bromide, and ethyl-iodide all of which may be prepared by methods known to those skilled in the art.

In practicing the method of the invention, the instant compositions are administered by oral or nasal inhalation, oral inhalation being the preferred route. Inhalation therapy (aerosols and solution for nebulizers) combines the advantages of maintenance and moderately-acute stage therapy in one convenient dosage unit.

The daily dose requirements vary with the particular compositions being employed the severity of the symptoms being presented, and the animal being treated. The dosage varies with the size of the animal. With large animals (about 70 kg. body weight), by the oral inhalation route, with for example, a hand nebulizer or a pressurized aerosol dispenser, the dose is from about 50 micrograms to about 5 milligrams, and preferably from about 100 micrograms to about 2 milligrams, approximately every 4 hours, or as needed.

For administration by the oral or nasal inhalation route with conventional nebulizers or by oxygen aerosolization it is convenient to provide the instant active ingredients suspended or dissolved in a pharmacologically acceptable inhalation carrier. Examples of such carriers are distilled water, water/ethanol mixtures, and physiological saline solution; other such carriers will suggest themselves to those skilled in the art. Entirely conventional additives may be employed in these dosage forms to stabilize or to provide isotonic media; for example, sodium chloride, sodium citrate, glucose, citric acid, sodium bisulfite, and the like can be employed. For convenience, the instant active ingredients are provided, preferably at concentrations of about 1 part of medicament to from about 20 to about 100 parts by weight of total mixture.

For administration as a self-propelled dosage unit for administering the active ingredient in aerosol form suitable for inhalation therapy, the composition can comprise the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can also be used a dispersing agent such as oleyl alcohol. Suitable means to employ the aerosol inhalation therapy technique are described, for example, in U.S. Pat. Nos. 2,868,691 and 3,095,355.

The following examples further illustrate the best mode contemplated by the inventors for the practice of the invention.

EXAMPLE 1

Anesthetized (Pentobarbitol-urethane) guinea pigs were artificially respired at a constant positive air pressure (Starling miniature pump) and changes in tidal air during inspiration were recorded, according to the method of Rosenthale et al., Int. Arch. Pharmacol., 172, 91 (1968). The bronchoconstrictor agents acetylcholine and histamine were administered intravenously at doses of 1 to 30 μg/kg. depending on each animal's sensitivity to these compounds, and control responses to acetylcholine and histamine were thus established. Bronchoconstrictor agents raise the resistance of the lungs to inflation thereby decreasing the tidal air flow. A solution of the test compound was then administered by aerosol, in physiological saline or distilled water, and the animals were then challenged again with acetylcholine or histamine and the degree of inhibition of bronchoconstriction by the test compound was thus determined.

Results

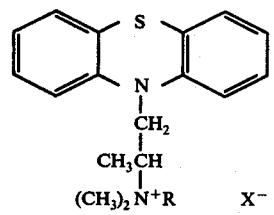

| R | X | Dose (μg as cation) in solvent* | No. Pigs | Mean % Inhibition (±S.E.) vs. Acetylcholine | Mean % Inhibition (±S.E.) vs. Histamine |
|---|---|---|---|---|---|
| $CH_3$ | I | 0.15 s | 7 | 16.86 (4.58) | — |
|  |  | 1.5 s | 8 | 62.38 (4.67) | — |
|  |  | 15.0 s | 4 | 99.0 (1.0) | — |
| $CH_3$ | I | 0.15 s | 6 | — | 15.33 (6.96) |
|  |  | 1.5 s | 4 | — | 49.0 (11.14) |
|  |  | 15.0 s | 2 | — | 97.5 |
| $CH_3$ | I | 0.15 s | 4 | 2.0 (1.23) | — |
|  |  | 1.5 s | 4 | 62.75 (11.89) | — |
|  |  | 15.0 s | 3 | 99.3 (0.67) | — |
| $CH_3$ | I | 15.0 s | 3 | — | 98.66 (1.33) |
| $CH'_3$ | I | 15.0 s | 2 | 97 | — |
|  |  | 15.0 s | 2 | — | 82 |
| $CH''_3$ | I | 15.0 s | 2 | 81 | — |
|  |  | 15.0 s | 3 | — | 95 (4.66) |
| $CH_3$ | I | 0.15 w | 5 | 20.0 (13.38) | — |
|  |  | 1.5 w | 5 | 47.0 (7.59) | — |
|  |  | 15.0 w | 3 | 98.66 (1.33) | — |
| $CH_3$ | I | 15.0 w | 3 | — | 98.0 (1.0) |
| $CH_3$ | Br | 0.15 w | 4 | 0 | — |
|  |  | 1.5 w | 4 | 38.75 (9.26) | — |
|  |  | 15.0 w | 3 | 99.0 (1.0) | — |
| $CH_3$ | Cl | 0.15 w | 4 | 15.0 (11.90) | — |
|  |  | 1.5 w | 4 | 24.25 (10.21) | — |
|  |  | 15.0 w | 3 | 86.3 (10.37) | — |
| $CH_3$ | Cl | 0.15 w | 3 | 2.0 (1.0) | — |
|  |  | 1.5 w | 3 | 26.67 (6.77) | — |
|  |  | 15.0 w | 3 | 100 (0) | — |
| $CH_3$ | $NO_3$ | 0.15 w | 4 | 12.0 (6.26) | — |
|  |  | 1.5 w | 4 | 43.5 (10.33) | — |
|  |  | 15.0 w | 3 | 100 (0) | — |
| $CH_3$ | $CH_3SO_4$ | 15.0 s | 2 | 86 | — |
|  |  | 15.0 s | 2 | — | 98 |
| $C_2H_5$ | I | 0.15 w | 4 | 20.0 (7.70) | — |
|  |  | 1.5 w | 4 | 62.75 (10.63) | — |
|  |  | 15.0 w | 3 | 98.66 (1.33) | — |
| $C_2H_5$ | I | 15.0 w | 3 | — | 78.67 (8.74) |
| $CH_3$ | Cl | 15.0 w | 4 | — | 98.2 (1.8) |
| n-$C_3H_7$ | I | 0.15 w | 4 | 5.5 (3.20) | — |
|  |  | 1.5 w | 4 | 43.75 (6.51) | — |
|  |  | 15.0 w | 3 | 84.0 (6.56) | — |
| n-$C_3H_7$ | I | 15.0 w | 3 | — | 68.0 (8.14) |
| n-$C_4H_9$ | I | 0.15 w | 4 | 0 | — |

-continued

Results

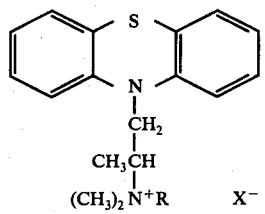

| R | X | Dose (μg as cation) in solvent* | No. Pigs | Mean % Inhibition (±S.E.) vs. Acetylcholine | Mean % Inhibition (±S.E.) vs. Histamine |
|---|---|---|---|---|---|
|   |   | 1.5 | w 4 | 39.25 (2.53) | — |
|   |   | 15.0 | w 3 | 52.0 (6.35) | — |
| n-C$_4$H$_9$ | I | 15.0 | w 3 | — | 66.33 (2.96) |

' = d-isomer
" = l-iosmer
* s-physiological saline; w=distilled water

EXAMPLE 2

A composition is prepared comprising dl-trimethyl[1-methyl-2-(phenothiazin-10-yl)ethyl]ammonium chloride in physiological saline solution, for administration of relieve bronchial spasm by oral inhalation with a hand nebulizer. In animals of from about 20 to about 80 kg. body weight, three to five inhalations of a solution containing 1 part medicament to from 20 to about 100 parts by weight of total mixture are used every 4 hours.

EXAMPLE 3

The procedure in U.S. Pat. No. 2,868,691 is used to prepare the instant compositions in self-propelling dosage unit forms.

"A suitable measured quantity of the medicament is mixed with, and dissolved in, a measured amount of the cosolvent. A stabilizer, if desired, is added. A measured quantity of the resulting solution is then introduced into an open container. The open container and its contents are then cooled, preferably to a temperature below the boiling point of the propellant to be employed. A temperature of −25° F. is usually satisfactory. A measured quantity of the liquified propellant which also has been cooled below its boiling point is then introduced into the container and mixed with the solution already present. The quantities of the components introduced into the container are calculated to provide the desired concentration in each of the final compositions. Without permitting the temperature of the container and its contents to rise above the boiling point of the propellant, the container is sealed with a closure equipped with a suitable dispensing valve arrangement. Upon warming to room temperature the contents of the container are mixed by agitation of the container to insure complete solution of the medicament. The sealed container is then ready to dispense the composition and provide the medicament in aerosol form."

EXAMPLE 4 dl-Trimethyl[1-Methyl-2-(Phenothiazine-10-yl)Ethyl]-Ammonium Methyl Sulfate dl-Promethazine hydrochloride (30 g.) was converted to the free base and was dissolved in absolute acetone and dimethyl sulfate (10 g.) was added (this is less than are equivalent of dimethyl sulfate due to its hazardous nature). After standing overnight, the solution was heated on a steam bath and cooled. The precipitated solid was filtered, washed with tetrahydrofuran and ether to provide dl-trimethyl[1-methyl-2-(phenothiazine-10-yl)ethyl]ammonium methyl sulfate, 27.6 g., m.p. 170°–173° C.

Analysis for: $C_{19}H_{20}N_2S_2O_4$: Calculated: C, 55.52; H, 6.35; N, 6.82. Found: C, 55.82; H, 6.49; N, 6.82.

EXAMPLE 5 l-Trimethyl[1-Methyl-2-(Phenothiazine-10-yl)Ethyl]-Ammonium Iodide dl-Promethazine hydrochloride (80 g.) was converted to the free base (75.3 g.) and was dissolved in absolute ethanol (275 ml.) and dibenzoyl-l-tartaric acid, monohydrate (103.0 g.) in alcohol (411 ml.) was added. The solution was allowed to stand overnight and the precipitated salt was filtered and washed with ethanol, then ether to give 82.0 g. of the salt, m.p. 131°–132° C., $[\alpha]_D^{25} = +61.05°$, (C=3, MeOH). Conversion of the salt back to the free base via aqueous NaOH/ether gave l-promethazine (34.1 g.) as a gum. l-Promethazine (25 g.) was dissolved in absolute acetone and methyl iodide was added (14.2 g.). On standing overnight l-trimethyl[1-methyl-2-(phenothiazin-10-yl)ethyl]ammonium iodide was collected by filtration (25.725 g.), m.p. 235°–238° C., $[\alpha]_D^{25} = +8.34°$, (C=3, MeOH).

Analysis for: $C_{18}H_{23}N_2SI$: Calculated: C, 50.74; H, 5.44; N, 6.57. Found: C, 50.75; H, 5.51; N, 6.80.

EXAMPLE 6 dl-Trimethyl[1-Methyl-2-(Phenothiazin-10-yl)Ethyl]-Ammonium Chloride dl-Promethazine was dissolved in acetone which had previously been saturated with methyl chloride at 0° C. This mixture was refluxed for 7 hours using a dry ice-/acetone condenser. During this time dl-trimethyl[1-methyl-2-(phenothiazin-10-yl)ethyl]ammonium chloride (11.5 g.), m.p. 238°–241° C. separated from the reaction mixture. This material was collected by filtration and recrystallized from ethanol/diethyl ether yielding 8.9 g. of product melting 248°–250° C.

Analysis for: $C_{18}H_{23}N_2ClS \cdot H_2O$: Calculated: C, 61.26; H, 7.14; N, 7.94; Cl, 10.04. Found: C, 61.56; H, 7.04; N, 7.94; Cl, 10.17.

EXAMPLE 7 dl-Trimethyl[1-Methyl-2-(Phenothiazin-10-yl)Ethyl]-Ammonium Nitrate dl-Trimethyl[1-methyl-2-(phenothiazin-10-yl)ethyl]-ammonium chloride (7.79 g., 0.022 mol.) and silver nitrate (3.39 g., .022 mol.) were added to water (200 cc.) and heated in solution at which time a colloidal suspension was formed. The mixture was allowed to stand at room temperature overnight filtered and the filtrate evaporated. The residue was dissolved in ethanol (150 cc.), treated with charcoal and filtered. The filtrate was diluted with petroleum ether producing a white solid which was collected by filtration. This solid was recrystallized from ethanol/petroleum ether yielding dl-trimethyl[1-methyl-2-(phenothiazin-10-yl)ethyl]ammonium nitrate (6.6 g.), m.p. 205°–207° C.

Analysis for: $C_{18}H_{23}N_3O_3S$: Calculated: C, 59.81; H, 6.41; N, 11.62. Found: C, 59.34; H, 6.43; N, 11.61.

EXAMPLE 8 dl-Trimethyl[1-Methyl-2-(Phenothiazin-10-yl)Ethyl]-Ammonium Bromide

Methyl bromide was bubbled into acetone (200 cc.) for 20 minutes and dl-promethazine (5 g.) was added. The reaction mixture was heated at reflux with a dry ice/acetone condenser for 2 hours at which time a solid had precipitated (6 g.) m.p. 222°–230° C. The product was recrystallized from ethanol/petroleum ether yielding dl-trimethyl[1-methyl-2-(phenothiazin-10-yl)ethyl]-ammonium bromide (5.8 g.), m.p. 237°–238° C.

Analysis for: $C_{18}H_{23}N_2SBr.H_2O$: Calculated: C, 54.41; H, 6.34; N, 7.05; S, 8.07. Found: C, 54.69; H, 5.98; N, 6.96; S, 8.69.

EXAMPLE 9 dl-N-Ethyl-N,N,α-Trimethyl-10H-Phenothiazine-10-Ethanaminium Iodide (dl-Promethazine Ethyl Iodide)

Ethyl iodide (10.9 g.) and dl-promethazine (10 g.) are heated in acetone (300 cc.) at reflux for 7 hours. The reaction mixture is concentrated under reduced pressure and the residue is recrystallized from ethanol/petroleum ether yielding dl-N-ethyl-N,N,α-trimethyl-10H-phenothiazine-10-ethanaminium iodide (dl-promethazine ethyl iodide) (7.6 g.), m.p. 179°–180° C.

Analysis for: $C_{19}H_{25}N_2SI$: Calculated: C, 51.82; H, 5.72; N, 6.36; S, 7.28. Found: C, 51.25; H, 5.80; N, 6.24; S, 7.34.

EXAMPLE 10 dl-N,N,α-Trimethyl-N-n-Propyl-10H-Phenothiazine-10-Ethanaminium Iodide (dl-Promethazine Propyl Iodide)

Promethazine (10 g., 0.035 mol.), and propyl iodide (8.5 g., 0.05 mol.) were dissolved in acetone (200 cc.), refluxed for 7 hours, and then taken to dryness. The residue was recrystallized from ethanol/petroleum ether yielding dl-N,N,α-trimethyl-N-n-propyl-10H-phenothiazine-10-ethanaminium iodide (dl-promethazine propyl iodide) (7.8 g.), m.p. 202°–204° C.(d).

Analysis for: $C_{20}H_{27}N_2SI$: Calculated: C, 52.86; H, 5.99; N, 6.16; S, 7.05. Found: C, 52.84; H, 6.02; N, 6.14; S, 6.95.

EXAMPLE 11 dl-N-n-Butyl,N,N,α-Trimethyl-10H-Phenothiazine-10-Ethanaminium Iodide (dl-Promethazine Butyl Iodide)

dl-Promethazine (10 g., .035 mol.) and n-butyl iodide were dissolved in acetone (250 cc.) refluxed for 7 hours and evaporated to dryness. The residual oil crystallized on standing, m.p. 175°–180° C. and was recrystallized from ethanol yielding dl-N-n-butyl,N,N,α-trimethyl-10H-phenothiazine-10-ethanaminium iodide (dl-promethazine butyl iodide) (6.1 g.), m.p. 180°–181° C.

Analysis for: $C_{21}H_{29}N_2SI$: Calculated: C, 53.84; H, 6.24; N, 5.98; S, 6.84. Found: C, 53.57; H, 6.12; N, 5.79; S, 6.75.

EXAMPLE 12

Cats of either sex were anesthetized and respiration was arrested by the administration of an intravenous infusion of 1 mg/ml/min of succinylcholine chloride. The animals were artificially respired with a Harvard pump. A neostigmine methylsulfate solution (0.1 mg/ml) was infused intravenously at a rate of 1 ml/min until maximal or complete bronchoconstriction occurred, but the experiment was not begun until a stable state was attained. The respiratory flow was measured with a Fleisch pneumotachograph and a differential pressure transducer. Transpulmonary pressure was measured with a differential pressure transducer bridged between the trachea and the intrapleural space. Pulmonary airway resistance and compliance was measured by a modification of the Mead & Whittenberger electronic subtraction method using the Hewlett-Packard respiratory pre-amplifier or the isovolumetric method using the Buxco Pulmonary mechanics computer [Rosenthale et al., J. Pharmacol. Exp. Ther., 178, 541, (1971)].

Drugs were administered as cation as an aerosol by means of a Monaghan ultrasonic nebulizer. The dosage was varied by adjusting the concentration of the solution. Activity was measured by the ability of the drug to reverse the increased airway resistance and decreased compliance characteristic of cholinergic stimulation induced by succinylcholine and neostigmine.

| EFFECT OF DRUGS ON CHOLINERGIC-INDUCED BRONCHOCONSTRICTION IN THE CAT[a] | | | | | |
|---|---|---|---|---|---|
| Compound | Number | | Pulmonary Resistance | Pulmonary Compliance | |
| Dose(μg) | Tests | Cats | % Protection | % Protection | Duration 50%[b] |
| (Promethazine methyl iodide) | | | | | |
| 0.1 | 6 | 2 | 14.3±1.1 | 5.8±3.6 | 6.7±3.2 |
| 1.0 | 7 | 3 | 39.4±2.1 | 3.7±.52 | 11.3±2.0 |
| 10.0 | 8 | 4 | 48.5±3.3 | 15.5±6.0 | 21.2±6.8 |
| 100.0 | 7 | 4 | 78.1±4.4 | 26.4±4.1 | 46.1±9.7 |
| (Promethazine methyl chloride) | | | | | |
| 0.1 | 5 | 5 | 8.8±7.7 | 6.8±4.1 | 2.7±1.5[c] |
| 1.0 | 11 | 10 | 17.2±2.8 | 7.8±4.1 | >10 |
| 10.0 | 5 | 5 | 50.0±4.6 | 71.4±51.1 | 21.0±4.0 |

-continued

| EFFECT OF DRUGS ON CHOLINERGIC-INDUCED BRONCHOCONSTRICTION IN THE CAT[a] | | | | | |
|---|---|---|---|---|---|
| Compound | Number | | Pulmonary Resistance | Pulmonary Compliance | |
| Dose(μg) | Tests | Cats | % Protection | % Protection | Duration 50%[b] |
| 100.0 | 5 | 5 | 72.8±2.1 | 60.8±25.7 | >60 |

[a] = Results are means ± S.E.
[b] = Time in minutes to return to 50% of control constricted state
[c] = Done in 3 cats The subject matter which the applicants regard as their invention is particularly pointed out and distinctly claimed as follows:

1. A method of relieving bronchial spasm and facilitating breathing in warm-blooded animals which comprises administering orally or nasally to a warm-blooded animal in need thereof, by aerosol route, an amount sufficient to relieve bronchial spasm and facilitate breathing in said warm-blooded animal of a composition comprising:
(a) a compound of the formula:

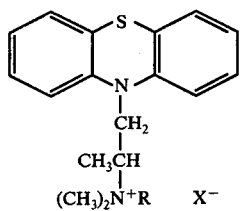

wherein R is cyclopropylmethyl or alkyl of from 1 to 4 carbon atoms; X is a pharmacologically acceptable anion; and
(b) a pharmacologically acceptable carrier.

2. The method of claim 1 which comprise administering to a warm-blooded animal in need thereof, by aerosol route, an amount sufficient to relieve bronchial spasm and facilitate breathing in said warm-blooded animal of a composition comprising:
(a) a compound of the formula:

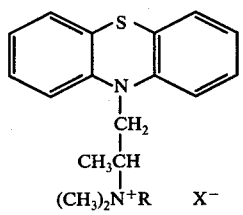

wherein R is cyclopropylmethyl or alkyl of from 1 to 4 carbon atoms; X is $OH^-$, $Cl^-$, $Br^-$, $I^-$, $NO^-_3$,

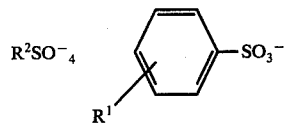

wherein $R^1$ is hydrogen, alkyl of from 1 to 6 carbon atoms, methoxy, chlorine, or bromine and wherein $R^2$ is alkyl of from 1 to 3 carbon atoms; and
(b) a pharmacologically acceptable carrier.

3. The method of claim 1 wherein R is $CH_3$.

4. The method of claim 1 wherein X is $Cl^-$.

5. The method of claim 1 wherein the compound in (a) is l-trimethyl[1-methyl-2-(phenothiazin-10-yl)ethyl]-ammonium iodide.

6. The method of claim 1 wherein the compound in (a) is d-trimethyl[1-methyl-2-(phenothiazin-10-yl)ethyl]ammonium iodide.

7. The method of claim 1 wherein the compound in (a) is dl-trimethyl[1-methyl-2-(phenothiazin-10-yl)ethyl]ammonium iodide.

8. The method of claim 1 wherein the compound in (a) is dl-trimethyl[1-methyl-2-(phenothiazin-10-yl)ethyl]ammonium chloride.

9. A bronchodilating and bronchial spasm reducing composition formulated for oral or nasal inhalation therapy comprising an aerosol consisting essentially of:
(a) a bronchodilating and bronchial spasm reducing amount of a compound of the formula:

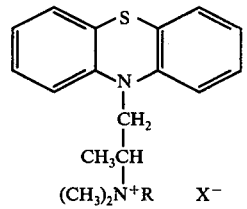

wherein R is cyclopropylmethyl or alkyl of from 1 to 4 carbon atoms; X is a pharmacologically acceptable anion; and
(b) a pharmacologically acceptable inhalation carrier.

10. The bronchodilating and bronchial spasm reducing composition of claim 9 comprising:
(a) a bronchodilating and bronchial spasm reducing amount of a compound of the formula:

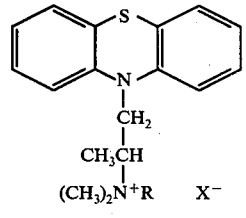

wherein R is cyclopropylmethyl or alkyl of from 1 to 4 carbon atoms; X is $OH^-$, $Cl^-$, $Br^-$, $I^-$, $NO^-_3$,

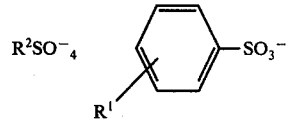

wherein $R^1$ is hydrogen, alkyl of from 1 to 6 carbon atoms, methoxy, chlorine, or bromine and wherein $R^2$ is alkyl of from 1 to 3 carbon atoms; and (b) a pharmacologically acceptable inhalation carrier, in an amount sufficient to provide a composition administerable by the oral inhalation route.

11. The composition of claim 9 wherein R is $CH_3$.

12. The composition of claim 9 wherein X is $Cl^-$.

13. The composition of claim 9 wherein the compound in (a) is dl-trimethyl[1-methyl-2-(phenothiazin-10-yl)ethyl]ammonium iodide.

14. The composition of claim 9 wherein the compound in (a) is d-trimethyl[1-methyl-2-(phenothiazin-10-yl)ethyl]ammonium iodide.

15. The composition of claim 9 wherein the compound in (a) is l-trimethyl[1-methyl-2-(phenothiazin-10-yl)ethyl]ammonium iodide.

16. The composition of claim 9 wherein the compound in (a) is dl-trimethyl[1-methyl-2-(phenothiazin-10-yl)ethyl]ammonium chloride.

* * * * *